US009546259B2

(12) United States Patent
Colle et al.

(10) Patent No.: US 9,546,259 B2
(45) Date of Patent: *Jan. 17, 2017

(54) POLYOL ESTER PLASTICIZERS AND PROCESS OF MAKING THE SAME

(71) Applicant: ExxonMobil Chemical Patents Inc., Baytown, TX (US)

(72) Inventors: Karla S. Colle, Magnolia, TX (US); Philippe L. Buess, Overijse (BE); Eddy T. Van Driessche, Eeklo (BE); Allen D. Godwin, Brenham, TX (US); Ramzi Y. Saleh, Baton Rouge, LA (US); Jon E. R. Stanat, Westhampton Beach, NY (US); Raphael F. Caers, Edegem (BE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/254,376

(22) Filed: Apr. 16, 2014

(65) Prior Publication Data

US 2014/0228494 A1 Aug. 14, 2014

Related U.S. Application Data

(62) Division of application No. 12/934,294, filed as application No. PCT/EP2009/053178 on Mar. 18, 2009, now abandoned.

(60) Provisional application No. 61/040,490, filed on Mar. 28, 2008, provisional application No. 61/040,480, filed on Mar. 28, 2008.

(30) Foreign Application Priority Data

May 8, 2008 (EP) .................................... 08155849
Jun. 17, 2008 (EP) .................................... 08158375

(51) Int. Cl.
| | |
|---|---|
| *C08K 5/103* | (2006.01) |
| *C08K 5/11* | (2006.01) |
| *C07B 41/12* | (2006.01) |
| *C07C 45/50* | (2006.01) |
| *C07C 51/235* | (2006.01) |
| *C07C 67/08* | (2006.01) |
| *C07C 69/30* | (2006.01) |
| *C08K 5/00* | (2006.01) |
| *C08K 5/12* | (2006.01) |

(52) U.S. Cl.
CPC .............. *C08K 5/11* (2013.01); *C07B 41/12* (2013.01); *C07C 45/50* (2013.01); *C07C 51/235* (2013.01); *C07C 67/08* (2013.01); *C07C 69/30* (2013.01); *C08K 5/0016* (2013.01); *C08K 5/103* (2013.01); *C08K 5/12* (2013.01)

(58) Field of Classification Search
CPC ....................................................... C08K 5/103
USPC ......................................................... 524/312
See application file for complete search history.

(56) References Cited

U.S. PATENT DOCUMENTS

| | | | |
|---|---|---|---|
| 3,787,459 A | 1/1974 | Frankel | |
| 5,248,531 A | 9/1993 | Nagai et al. | |
| 6,307,093 B1 | 10/2001 | Godwin et al. | |
| 6,652,774 B2 | 11/2003 | Zhou et al. | |
| 6,734,241 B1 | 5/2004 | Nielsen et al. | |
| 6,740,254 B2 | 5/2004 | Zhou et al. | |
| 6,777,514 B2 | 8/2004 | Patil et al. | |
| 6,811,722 B2 | 11/2004 | Zhou et al. | |
| 7,297,728 B2 | 11/2007 | Yamamoto et al. | |
| 7,297,738 B2 | 11/2007 | Gosse et al. | |
| 7,323,588 B2 | 1/2008 | Grass et al. | |
| 8,163,825 B2 * | 4/2012 | Colle et al. .................. | 524/312 |
| 8,299,281 B2 | 10/2012 | Dakka et al. | |
| 8,476,350 B2 | 7/2013 | Dakka et al. | |
| 2001/0021429 A1 * | 9/2001 | Nizuka ................. | A61L 29/041 428/36.9 |
| 2002/0019559 A1 | 2/2002 | Brunner et al. | |
| 2003/0116750 A1 | 6/2003 | Zhou et al. | |
| 2006/0247461 A1 | 11/2006 | Schlosberg et al. | |
| 2007/0299277 A1 | 12/2007 | Tustin et al. | |

(Continued)

FOREIGN PATENT DOCUMENTS

| | | |
|---|---|---|
| WO | WO 99/32427 | 7/1999 |
| WO | WO 03/029339 | 4/2003 |

(Continued)

OTHER PUBLICATIONS

Keil, W., "Zur Kenntnis der Fette aus Fettsäuren mit ungerader Kohlenstoffatomzahl," Hoppe-Syler's Zeitschrift für Physiologische Chemie, vol. 282 (1947), pp. 137-142 (Abstract Only).

(Continued)

*Primary Examiner* — Tae H Yoon
(74) *Attorney, Agent, or Firm* — Nancy T. Krawczyk; Luke A. Parsons

(57) ABSTRACT

Triglyceride and other polyol ester PVC plasticizers can be produced by recovery of branched C6 to C9 aldehydes from a hydroformylation product, optional hydrogenation to the alcohol, oxidation to the acid with oxygen and/or air, recovery of the resulting acid, and esterification with glycerol, ethylene glycol, propylene glycol or mixtures thereof. The branched alkyl chains comprise at least 10% methyl branching. Special triglycerides are derived from branched aliphatic acids having alkyl chains with average carbon numbers from 6 to 9 and at least 10% methyl branching. These triglycerides are fast fusing plasticizers if before esterification with glycerol, an aryl acid is introduced together with the aliphatic acids.

13 Claims, 1 Drawing Sheet

(56) References Cited

U.S. PATENT DOCUMENTS

2010/0159177 A1* 6/2010 Dakka et al. ............... 428/36.9
2010/0298477 A1 11/2010 Godwin
2010/0305250 A1 12/2010 Colle et al.

FOREIGN PATENT DOCUMENTS

| WO | WO 2004/046078 | 6/2004 |
| WO | WO 2006/077131 | 7/2006 |
| WO | WO 2006/109984 | 10/2006 |
| WO | WO 2008/084046 | 7/2008 |
| WO | WO 2008/121847 | 10/2008 |
| WO | WO 2009/070398 | 6/2009 |
| WO | WO 2009/070399 | 6/2009 |

OTHER PUBLICATIONS

Sears et al., "*Technology of Plasticizers,*" 1982, John Wiley & Sons, pp. 95-99.

Baykut et al., "*The Synthesis of Mono- and Triglycerides of Branched Fatty Acids and Physical Properties of the Synthesized Glycerides,*" Chimica Acta Turcica, vol. 5 (1977), pp. 93-101.

Godwin, A. D., "*Plasticizers,*" Applied Polymer Science 21$^{st}$ Century, C. D. Craver and C. E. Carraher, Eds., Elsevier (2000), pp. 157-175.

Manninen et al., "*2-Ethylhexanoic Acid Inhibits Urea Synthesis and Stimulates Carnitine Acetyltransferase Activity In Rat Liver Mitochondria,*" Archives of Toxicology (1989), 63(2), pp. 160-161.

Riser et al., "*A Method for Determining Compatibility Parameters of Plasticizers for Use in PVC Through Use of Torsional Modulus,*" Polymer Engineering and Science, Apr. 1967, pp. 110-114.

Shobha et al., "*Structural Expressions of Long-Chain Esters on Their Plasticizing Behavior in Poly(vinyl Chloride)*", Macromolecules 1992, 25, pp. 6765-6769.

* cited by examiner

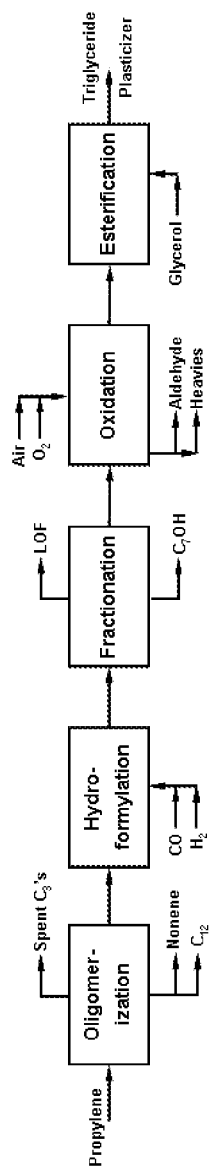

POLYOL ESTER PLASTICIZERS AND PROCESS OF MAKING THE SAME

CROSS-REFERENCE TO RELATED APPLICATIONS

This application is a divisional of and claims priority to U.S. patent application Ser. No. 12/934,294, filed on Sep. 24, 2010, which claims priority to and the benefit from 371 National Stage Application of PCT/EP2009/053178, filed Mar. 18, 2009, which claims the benefit of U.S. Provisional Application No. 61/040,490, filed Mar. 28, 2008; U.S. Provisional Application No. 61/040,480, filed Mar. 28, 2008; EP 08155849.6, filed May 8, 2008; and EP 08158375.9, filed Jun. 17, 2008, all of which are incorporated herein by reference in their entireties.

FIELD OF THE INVENTION

The invention relates to triglyceride esters based on branched alkyl groups, useful as plasticizers and viscosity depressants for a wide range of resins. The invention further relates to a process for producing polyol ester plasticisers from carboxylic acids having branched alkyl chains, obtained by hydroformylation. The polyol esters may also comprise an aromatic acid group.

BACKGROUND OF THE INVENTION

Plasticizers are incorporated into a resin (usually a plastic or elastomer) to increase the flexibility, workability, or distensibility of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, poly (vinylidene chloride), nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

Plasticizers can be characterized on the basis of their chemical structure. The most important chemical class of plasticizers is (ortho-)phthalic acid esters, which accounted for about 85% worldwide of PVC plasticizer usage in 2002. However, in the recent past there as been an effort to decrease the use of phthalate esters as plasticizers in PVC, particularly in end uses where the product contacts food, such as bottle cap liners and sealants, medical and food films, or for medical examination gloves, blood bags, and IV delivery systems, flexible tubing, or for toys, and the like. For these and most other uses of plasticized polymer systems, however, a widely accepted substitute for phthalate esters has heretofore not materialized.

One such suggested substitute for phthalates are esters based on cyclohexanoic acid. In the late 1990's and early 2000's, various compositions based on cyclohexanoate, cyclohexanedioates, and cyclohexanepolyoate esters were said to be useful for a range of goods from semi-rigid to highly flexible materials. See, for instance, WO 99/32427, WO 2004/046078, WO 2003/029339, WO 2004/046078, U.S. Application No. 2006-0247461, and U.S. Pat. No. 7,297,738.

However, one of the problems with plasticizers based on esters of cyclohexanoic acid is processability, particularly the fusion characteristics. When a plasticized product is produced, such as a PVC product, the product should reach a temperature at some point during fabrication at which the polymer crystallites are melted. This is called the fusion temperature. In the case of PVC, depending upon the plasticizer, this temperature generally ranges from 160 to 180° C. Plasticizers which are better solvents for a given polymer will fuse at lower temperatures than those that are poorer solvents. Since many plasticized polymer products, such as flexible PVC products, are produced through continuous processes, those faster or stronger solvating plasticizers will arrive at this fusion temperature faster; hence the development of the descriptor "fast fusing" or "faster fusing". These same plasticizers are also known as strong solvating plasticizers. For most applications, the plasticizer reference standard is di-2-ethylhexyl phthalate (DEHP) as this plasticizer has been the most widely used plasticizer world wide since it was commercialized in the late 1930's. Plasticizers which fuse at lower temperatures than that required for DEHP, at the same concentration in a given polymer system, are considered fast fusing plasticizers. Likewise, plasticizers that fuse at higher temperatures than that required for DEHP, at the same concentration in a given polymer system, are considered "slow fusing" plasticizers.

It has been proven to be particularly difficult to identify, develop and commercialize a widely accepted fast fusing plasticizer substitute for phthalate esters. Fast fusing plasticizers are defined in more detail further in this document.

Fast fusing plasticizers are valued in the production of many flexible articles, particularly flexible PVC articles. See, for instance, U.S. Pat. No. 7,297,728. Fast fusing plasticizers based on non-phthalates are also known. For instance, the present inventors have recently described, along with others, fast fusing plasticizers based on cyclohexanoic acid esters of C4-C7 secondary alcohols (see copending application PCT/US2008/080891, filed Oct. 23, 2008), plasticizers based on cyclohexanoic acid esters of C7-C12 secondary alcohols (see copending application PCT/US2008/080893, filed Oct. 23, 2008), and also coplasticizer systems based on cyclohexanoic acid esters and non-phthalate fast fusing plasticizers. See also U.S. Pat. No. 7,323,588.

Other suggested substitutes for phthalates as plasticisers include esters based on benzoic acid (see, for instance, U.S. Pat. No. 6,740,254 or WO 2006/077131) and polyketones, such as described in U.S. Pat. No. 6,777,514; and also in WO 2008/121847. Epoxidized soybean oil, which has much longer alkyl groups (C16 to C18) has been tried as a plasticizer, but is generally used as a PVC stabilizer. Stabilizers are used in much lower concentrations than plasticizers.

Typically, the best that has been achieved with substitution of the phthalate ester with an alternative material is a flexible PVC article having either reduced performance or poorer processability. Thus, heretofore efforts to make phthalate-free plasticizer systems for PVC have not proven to be entirely satisfactory, and this is still an area of intense research.

Triglycerides produced from branched C6 to C9 acids have been studied in the past, but primarily in other technical fields and the studies have been rather limited in scope. W. Keil, in "Zur Kenntnis der Fette aus Fettsäuren mit ungerader Kohlenstoffatomzahl", Hoppe-Seyler's Zeitschrift für Physiologische Chemie, vol. 282, 1947, pages 137-142 studied the metabolites of a triglyceride of 2-propyl pentanoic acid and of 3-propyl hexanoic acid when fed to dogs, by urine analysis. A. Aydin et al., in "The synthesis of mono- and triglycerides of branched fatty acids and physical properties of the synthesized glycerides.", Chimica Acta Turcica, vol. 5, 1977, pages 93-101, determined physical properties of 2-ethyl hexanoic acid and of 2-propyl hexanoic acid, and predicted usefulness of such triglycerides in numerous future applications in various fields of industry, more specifically in textile industry as softening material in sanforization, i.e. a mechanical shrinking process for fabrics before these are manufactured into articles such as clothing, in cosmetic formulations and in the food industry.

Polyol esters of branched C6 to C9 acids are known as lubricants and lubricant components. A. D. Godwin et al. in U.S. Pat. No. 6,307,093 disclose in col. 12 as useful in this field the esters of branched C9 acids with pentaerythritol, di(pentaerythritol), tri(pentaerythritol); trimethylolethane, trimethylolpropane, trimethylolbutane, and dimers and trimers thereof, and neopentylglycol.

Plasticizers based on triglycerides have been tried in the past, based on natural triglycerides from various vegetable oils. The alkyl groups on these natural triglycerides are linear, and the products can be incompatible when the alkyl chain is too long.

"Structural Expressions of Long-Chain Esters on Their Plasticizing Behavior in Poly(vinyl Chloride)", H. K. Shobha and K. Kishore, Macromolecules 1992, 25, 6765-6769, reported the influence of branching and molecular weight in long-chain esters in PVC. Triglycerides (TGE's) having linear alkyl groups were studied.

"A Method for Determining compatibility Parameters of Plasticizers for Use in PVC Through Use of Torsional Modulus", G. R. Riser and W. E. Palm, Polymer Engineering and Science, April 1967, 110-114, also investigate the use of triglycerides and their plasticizing behavior with PVC, including tri-iso-valerin (3-methyl butanoate) triglyceride. It was reported that "these materials have volatilities that are much too high for good long-time permanence".

Nagai et al. in U.S. Pat. No. 5,248,531, teaches the use of articles comprising vinyl chloride-type resins (among others) using triglyceride compounds as a hemolysis depressant, and also comprising 10 to 45 wt % of plasticizers selected from trialkyl trimellitates, di-normal alkyl phthalates, and tetraalkyl pyromellitates. The alkyl chains of the acid moiety $R^1$-$R^3$ in the structure below, formula (I), are independently an aliphatic hydrocarbon group of 1 to 20 carbon atoms and in embodiments at least one of the alkyl chains is branched. One specific triglyceride disclosed is glyceryl tri-2-ethylhexanoate, having the following formula (I).

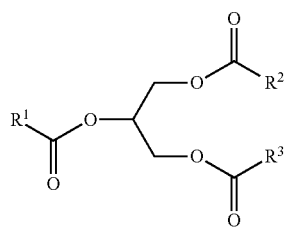

(I)

Zhou et al. discloses, in U.S. Pat. Nos. 6,652,774; 6,740,254; and 6,811,722; phthalate-free plasticizers comprising a mixture of different triesters of glycerin, formed by a process of esterifying glycerin with a mixture comprising a mixture of alkyl acids and aryl acids. A triglyceride ester produced from a 50/50 mixture of 2-ethyl-hexanoic acid and benzoic acid is exemplified. It was found to be compatible with PVC resin, while glyceryl tribenzoate and glyceryl tri(2-ethyl) hexanoate are stated in paragraph [0020] to be known as being incompatible in such resin.

Nielsen et al., in U.S. Pat. No. 6,734,241, teach a composition comprising a thermoplastic polymer as in formula (I) above, wherein at least one of the R groups is a short alkyl group having from 1-5 carbon atoms and at least one of the R groups is a saturated branched alkyl group having from 9 to 19 carbon atoms and also having a hydrophilic group.

U.S. Pat. No. 6,740,254 mentions plasticizer esters based on C4 and benzoic acids.

However, the prior art has not recognized the advantages of using esters, including triglycerides, based on polyols together with particularly selected branched alkyl acids as plasticizers, and in combination with aryl acids as fast fusing plasticizers. The latter may be used with other slower fusing plasticizers in plastics systems. It was stated already hereinbefore that the TGE of 2-ethyl hexanoic (2EH) acid has a problem of compatibility with PVC. A particular problem with esters from alkyl acids having an ethyl branch on the second carbon is a toxicity concern. An ester, when introduced into a living organism such as a human or an animal, may become at least partly hydrolysed. The ester hydrolysis liberates the acid. When the ester comprises high amounts of the 2-ethyl hexyl moiety on the acid alkyl group, 2-ethyl hexanoic acid is liberated in significant amounts in the living organism, which is undesirable because of the toxicity concern associated with this specific acid (Manninen et al, 1989, Archives of Toxicology 63(2), pages 160-1). This effect may be attributed to the specificity of the ethyl branch on the second carbon, and the concern may therefore also relate to other acids having that branch in that location.

Among the problems presented by the aforementioned triglycerides is they cannot be made conveniently and thus generally are quite expensive and/or are specialty chemicals not suitable as replacements for phthalates from an economic standpoint and/or are not as compatible with the range of polymer systems that phthalates are compatible with, and thus are not viable general purpose replacements for phthalates from a physical property standpoint.

For instance, some synthesis methods involve at least two separate steps, such as where the glycerol is first partially esterified with the C10 to C20 branched chain acyl group and then reacted with acetic acid or acetic anhydride.

Other syntheses involving mixed acid feeds will require addition of a hydrocarbon solvent for azeotropic distillation of the water to drive the esterification reaction to completion (as measured by the hydroxyl number of the ester, which is a measure of the amount of unreacted OH groups), due to the spread in boiling points between the mixed acids. In addition, the use of mixed acid feedstock such as cited in Zhou et al. and in Nielsen et al. can increase the process complexity when recycling unreacted acids.

Triglycerides based on acids derived from natural products will be limited to naturally occurring linear alkyl groups with even carbon numbers, which offer very little flexibility in designing an appropriate plasticizer system for a given polymer system.

Thus what is needed is a method of making a general purpose non-phthalate plasticizer having high throughput and providing a plasticizer having suitable melting or pour point, increased compatibility, good general purpose performance and low temperature properties.

The present inventors have surprisingly discovered that triglyceride and or glycol esters, produced by esterification of glycerol, ethylene glycol or propylene glycol with acids derived from the hydroformylation of olefins and subsequent oxidation of the oxygenate to a branched C6 to C9 acid, provide for polyol esters having appropriately branched alkyl groups for providing compatibility with a wide variety of resins and which are obtainable with a high throughput. Esterification of glycerol using an acid mixture with a narrow carbon number range eliminates many of the aforementioned problems, and enables high yield of the glycerol triesters to be obtained, having low residual hydroxyl numbers.

SUMMARY OF THE INVENTION

The invention is firstly directed to a process for the production of a polyol ester comprising: (i) the formation of at least one branched C6 to C9 aldehyde employing a process comprising a hydroformylation step; (ii) the formation of a branched C6 to C9 acid by oxidizing the branched C6 to C9 aldehyde to the acid or by first hydrogenating the branched C6 to C9 aldehyde to a branched C6 to C9 alcohol and subsequently oxidizing the branched C6 to C9 alcohol to the acid; and (iii) the esterification of the branched C6 to C9 acid with a polyol selected from glycerol, ethylene glycol, propylene glycol and mixtures thereof. The oxidation steps are preferably performed with oxygen and/or air. The branched C6 to C9 aldehyde, and consequently also the branched C6 to C9 alcohol and the C6 to C9 branched acid derived therefrom, is preferably characterised by having an average branching of from 0.5 to 3.0 branches per molecule and at least 10% of the branches being methyl branches.

The polyol esters according to the invention are plasticizers which may have a suitable melting or pour point, increased compatibility, good general purpose performance and low temperature properties. Due to the moderate degree of branching of the alkyl chains, they provide advantages over their unbranched equivalents by a lower plasticizing efficiency, providing an advantage of lower cost and lower weight to the plasticized PVC product, by a higher PVC compatibility and extender tolerance, a slower migration, a greater resistance to chemical hydrolysis and a greater resistance to biodegradation. As compared to their more highly branched equivalents, they provide advantages by a reduced viscosity, also when used in a plastisol, a reduced vapor pressure and hence volatility, an improved cold flex performance, a higher thermo-oxidative stability and an increased photostability.

The process according to the invention, in another embodiment, comprises the addition of an aromatic acid into the esterification step, the aromatic acid being selected from the group consisting of benzoic acid, 2-methyl benzoic acid, 3-methyl benzoic acid, 4-methyl benzoic acid, 4-tert-butyl benzoic acid, or mixtures thereof.

The invention is also directed to the product of the process of the invention, which comprises a triglyceride as represented by the formula (I) above, wherein at least one of the R1, R2, and R3 groups defining the acids in the triglyceride, is independently selected from C4 to C9 alkyl groups, whereby, if at least one of a C4 or a C9 alkyl group is present, this C4 or C9 group is present in a mixture of aliphatic acids, and whereby the mixture of aliphatic acids has an average carbon number of at least 6 and at most 9, with the proviso that the average branching on the alkyl groups of the aliphatic acids is from 0.5 to 3.0 branches per molecule, and wherein at least 10% of the branches on the alkyl groups of the aliphatic acids are methyl branches. In an embodiment, the average branching may range from about 0.6 to about 2.2. In another embodiment, the average branching of the C5 to C8 alkyl groups ranges from about 0.7 to about 1.8, preferably around about 0.8 to about 1.6, more preferably about 1.2 to about 1.4 branches per molecule. In embodiments the average branching will be from about 1.1 to about 1.8. These averages are based on the sum total of alkyl groups on all R1-R3 side chains in all the polyols in the mixture, and are molar averages when determined by $^1$H-NMR as explained below. They should not include any branching that may be present on the aromatic acid, or the aromatic acid part of the polyol ester, should any such aromatic group be present.

The triglyceride according to the invention may bring special benefits in terms of efficiency, outdoor aging, and low temperature flexibility. In addition, it may be a potential substitute for a phthalate ester plasticisers, and may reduce a toxicity concern attributed to 2-ethyl branching.

The invention is also directed to a composition comprising the product of the process of the invention and a resin.

The invention is still further directed to an article comprising the composition according to the invention.

It is an object of the invention to provide a plasticizer suitable for diverse resins.

It is another object of the invention to provide a high throughput process for producing polyol esters, in particular triglycerides.

It is yet another object of the invention to provide phthalate-free compositions and articles.

These and other objects, features, and advantages will become apparent as reference is made to the following detailed description, preferred embodiments, examples, and appended claims.

BRIEF DESCRIPTION OF THE DRAWINGS

In the accompanying drawings, like reference numerals are used to denote like parts throughout the several views.

FIG. 1 is a schematic representation of a process according to a preferred embodiment of the invention.

DETAILED DESCRIPTION OF THE INVENTION

According to the invention, at least one polyol or triglyceride ester is produced by esterification of one or more branched C6 to C9 acids with glycerol, ethylene glycol, propylene glycol or with mixtures thereof. These polyol esters are useful as plasticizers for plastics. The esters, acids, alcohols and aldehydes in the present invention are typically mixtures of chemical compounds. These compounds may differ in isomer structure and may differ in carbon number. When the products or intermediates in the present invention are characterised that are mixtures, unless stated otherwise it is the average for the mixture that is specified.

In preferred embodiments, the process further comprises providing a higher olefin feed for the hydroformylation step from the dimerization or oligomerization of diverse lower olefin feedstocks, preferably the dimerization of a C3 or C4 feedstock, or a mixture thereof.

In an alternative embodiment, the branched C6 to C9 aldehyde is obtained by aldolisation of at least one C3 to C6 aldehyde as the product of the hydroformylation step, or mixtures thereof. Preferred is the aldolisation of propionaldehyde and a butyraldehyde, which may be isobutanal or n-butanal, to form a branched C7 aldehyde as the basis for the production of the corresponding branched C7 acid.

In this embodiment, the process may further comprise the formation of the C3 to C6 aldehyde by the hydroformylation of ethylene, propylene, a butylene, a pentene, or a mixture thereof.

In another version of this embodiment, one or more C5 aldehydes may be produced by the hydroformylation of a C4 olefin, and part of the C5 aldehyde(s) may be aldolised to form a C10 aldehyde. The C5 and/or the C10 aldehydes may then be converted to their respective C5 and/or C10 acids or acid mixtures. These acids may be used individually or in combination in a mixture of acids containing branched acids and having an average carbon number of at least 6 and at most 9, as the feedstock for a polyol ester according to the invention.

In the specific case of C7 triglycerides, the process of the invention provides, in preferred embodiments, an average branching of about 1.2±0.1, based on the branching in molecules having all C7 acid groups and thus having C6 alkyl chains in each of $R^1$, $R^2$ and $R^3$. In the specific case of C9 triglycerides, the process of the invention provides, in preferred embodiments, an average branching of about 3.0±0.1, based on the branching in molecules having all C9 acid groups and thus having C8 alkyl chains in each of $R^1$, $R^2$ and $R^3$. In a more preferred embodiment, there is a blend of triglycerides having a mixture of C7 and C9 acid groups and thus C6 and C8 alkyl chains on $R^1$, $R^2$ and $R^3$ resulting in an average branching of about 1.6±0.2, preferably 1.6±0.1.

The invention further concerns fast fusing plasticizers based on the esterification of polyols with aliphatic acids, benzoic acids, and mixtures thereof, preferably of mixtures of the branched C6 to C9 acids of the invention with an aryl acid such as benzoic acid or a substituted form thereof. The preferred polyol esters are triglycerides, and glycol esters of ethylene and propylene.

The invention also concerns fast fusing plasticizers based on the esterification of polyols with aliphatic acids, benzoic acids, and mixtures thereof.

The term "fast fusing plasticizer", as used herein, is defined as follows. Using the solution temperature for the C8 phthalate ester DEHP as the standard, those plasticizers with lower solution temperatures, at a given concentration and for a given polymer system, are described as "fast fusing plasticizers" or faster fusing plasticizers, while those with higher solution temperatures are considered "slow fusing plasticizers" or slower fusing plasticizers. This assumes that the plasticizer in question is the sole plasticizer in the polymer system.

The "solution temperature" is demonstrated through the use of a simple test procedure. In this test, 48 grams of the plasticizer to be tested is mixed with 2 grams of the polymer system, such as PVC resin, at room temperature. The mixture is slowly heated, with stirring, until the PVC resin dissolves. The temperature at which the polymer system, e.g., PVC resin dissolves in the plasticizer is recorded as the "solution temperature". More specifics of the experimental design are not necessary for one of ordinary skill in the art since the important factor is how the plasticizer performs in the experiment relative to DEHP. Other test procedures that can be used to evaluate fast fusing plasticizers are the hot bench plastisol gelation method and the dynamic mechanical analysis of plastisols, both per se well-known in the art.

The solution temperature testing procedure gives a solution temperature of 120° C. for DEHP. The 1,2-cyclohexanedicarboxylic acid of 2-ethylhexanol has a solution temperature of 130° C. The diisononyl ester of the same acid has a solution temperature of 139° C. and the diisodecyl ester has a solution temperature of 149° C. The C11 ester would have a solution temperature>160° C. Faster fusing plasticizers would have solution temperatures<120° C. by this test method, while slower fusing plasticizers would have solution temperatures>120° C.

Using the hot bench plastisol gelation method, which measures the temperature at which a PVC plastisol begins to gel, DEHP has a gelation temperature of 70° C. The 1,2 cyclohexanedicarboxylic acid of 2-ethylhexanol has a gelation temperature of 73° C. The diisononyl ester of the same acid has a gelation temperature of 78° C. and the diisodecyl ester has a gelation temperature of 87° C. The C11 ester would have a solution temperature>95° C. Using this test method, faster fusing plasticizers would have lower gelation temperatures, typically<70° C., while slower fusing plasticizers would have a higher gelation temperature, typically>70° C.

In preferred embodiments, the fast fusing plasticizers of the invention have both solution temperatures and hot bench gelation temperatures lower than those reported for di-ethylheptyl phthalate (DEHP).

Fast fusing plasticizers according to the invention may be used in the production of diverse articles such as flooring, toys, wall coverings, synthetic leather, carpet backing, and the like.

In preferred embodiment, these fast fusing plasticizers can be used in combination with other plasticizers such as di-isononyl phthalate, C7-C9 alkyl esters of cyclohexanepolycarboxylic acids, various acetylated citrate esters prepared from C4-C9 alcohols, and slow fusing esters based on polyols, to improve processability and appearance through reduced surface blemishes, and improved clarity.

In still more preferred embodiments, fast fusing plasticizers of the invention are used in combination with poorer processing plasticizers such as di-isononyl cyclohexanedicarboxylic acid esters, adipic acid esters of C8 to C10 aliphatic alcohols, polymeric plasticizers based on esters and polyesters of diacids and diols, even di-2-ethyl hexyl terephthalate, to provide a phthalate free product.

In embodiments, these fast fusing plasticizers, with or without the co-plasticizers, can be processed with various plastic systems, such as plastisols and extruded products.

In embodiments one or more of the fast fusing plasticizers based on acid esters of polyols are used in blends with general purpose plasticizers such as di-2-ethylhexyl phthalate (DOP or DEHP), and in other embodiments can be blended with poor processing plasticizer such as adipates, trimellitates, di-isononyl cyclohexanoate, polymeric plasticizers, and terephthalates such as di-2-ethylhexyl terephthalate (DOTP). Blending of different plasticizers is very common in the industry in order to obtain a compromise of properties that are considered advantageous compared to what may be achieved using a single plasticizer.

Fast fusing plasticizers can be prepared by the esterification of polyols such as glycerol, neopentyl glycol, trimethylol propane and pentaerythriol with a mixture of shorter chain C4-C9 aliphatic acids, aryl acids such as benzoic acid, and mixtures thereof. When aliphatic acids having C8+ chains, such as C9 or C10 acids, it is preferred to use these in admixture with an aryl acid. This improves the compatibility of the plasticiser with the resin.

For example the plasticizer of this invention prepared by the esterification of glycerol can be represented by the averaged formula:

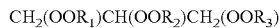

Where for $R_1$, $R_2$, and $R_3$, all three may be the same or different, or two of these may be different from the third. Each of these R groups will contain about 5, 6, 7, 8, 9 or 10 carbon atoms, with at least one of the R groups being branched alkyl and at least one possibly being aryl. In the case of the fast fusing plasticizers of this invention prepared from the esterification of glycerol with isoheptanoic acid as a branched C7 acid mixture, and benzoic acid, the resulting product will be a mixture of isomers according to glyceryl (1,3)-bisisoheptanoate benzoate, glyceryl (1,2)-bisisoheptanoate benzoate, glyceryl (1,2)-bisbenzoate isoheptanoate, glyceryl (1,3)-bisbenzoate isoheptanoate, glyceryl (1,2,3)-trisisoheptanoate, and glyceryl (1,2,3)-trisbenzoate. If a fast fusing plasticizer is prepared by the esterification of glycerol with a mixture of C6 and C7 aliphatic acids and benzoic acid, the number of possible isomers increases even further. In order to obtain the fast fusing properties required for that embodiment of this invention, the molar ratio of benzoic acid to C6 to C9 aliphatic acids needs be at least 1 to 8, more preferably at least 1 to 5, even more preferably at least 1:2, even more preferably 1:1. Although benzoic acid is the preferred aromatic acid, other aromatic acids such as 2-methyl benzoic acid, 3-methyl benzoic acid, 4-methyl benzoic acid, and 4-tert-butyl benzoic acid can be used.

The fast fusing plasticizers based on polyols esters of C4-C8 acids and/or benzoic acid may be supplemented with other fast fusing plasticizers such as hydrogenated forms of butyl benzyl phthalate (BBP), diisoheptyl phthalate, dihexyl phthalate, and dibutyl phthalate, and also dibutyl terephthalate, dibenzoate esters of diethylene glycol or dipropylene glycol, benzoate esters of C8 or C9 or C10 branched primary alcohols, various alkyl sulfonic acid esters of phenol, cyclohexanediacid esters of C4-C7 aliphatic secondary alcohols, acetyl tributyl citrate, acetyl trihexyl citrate, acetyl tripentyl citrate, acetyl triisopentyl citrate, and butyrl tributyl citrate.

Although the preferred plasticizer system of the invention is phthalate-free, in some cases it may be suitable to include certain amounts of phthalates, such as fast fusing plasticizers selected from butyl benzyl phthalate (BBP), diisoheptyl phthalate, dihexyl phthalate, dibutyl phthalate, and mixtures thereof.

In preferred embodiment, these fast fusing plasticizers can be used in combination with other plasticizers such as di-isononyl phthalate (DINP), di-isodecyl phthalate (DIDP), di-2-propyl heptyl phthalate (DPHP), di-2-ethylhexyl terephthalate (DOTP), di-isononyl cyclohexanedicarboxylic acid ester, acetylated citrate esters of C4, C5, C6, C8, or C9 aliphatic alcohols, and slower fusing esters based on polyols, to improve processability and appearance through reduced surface blemishes and improved clarity.

In still more preferred embodiments, fast fusing plasticizers of the invention are used in combination with poorer processing non-phthalate plasticizers such as di-isononyl cyclohexandioates, adipate esters, polymeric plasticizers, even di-2-ethylhexyl terephthalate, which, in preferred embodiments, provides a phthalate free product, which is the term used for products that are at least free of ortho-phthalates, i.e. in which the presence of ortho-phthalate esters is insignificant, such as at most 0.1% by weight, preferably at most 100 ppm by weight. More preferably, the products are also free of other phthalate esters, such as isophthalate or terephthalate esters.

In embodiments, these fast fusing plasticizers, with or without the co-plasticizers, can be processed with various plastic systems using plastisols, extruded products, coated fabrics, injection molded products, and products made through rotational molding.

Fast fusing plasticizers according to the invention may be used in the production of diverse articles such as flexible vinyl resilient flooring, toys, carpet tiles, shoes, chair mats, synthetic leather, wall paper, floor mats, road cones, tubing, and table cloths. In preferred embodiments, one or more of the fast fusing plasticizers is most commonly used in blends with general purpose plasticizers such as DEHP (di-2-ethylhexyl phthalate), DINP (di-isononyl phthalate), or DIDP (di-isodecyl phthalate). But the use of fast fusing plasticizers can be used to improve the processability of any poor processing plasticizer such as adipates, trimellitates, di-cyclohexanoates such as di-isononyl cyclohexanoate, polymerics, and DOTP.

By "short chain aliphatic acids" is meant straight or branched aliphatic acids containing C4 to C9 carbon atoms (including the carboxylic acid carbon), preferably C6-C9 acids, and mixtures thereof, preferably straight or branched chain C6-C8 carbon atoms, more preferably C7-C8 carbon atoms.

In embodiments, plasticizing systems of the invention may be essentially phthalate-free, meaning there may be some inevitable impurity of phthalates due to the process by which the esters are made (such as when the plasticizing system includes, in addition to the fast fusing plasticizers based on one or more acid esters of polyols with short chain aliphatic acids, benzoic acid, or mixtures thereof, also one or more cyclohexanecarboxylic acid esters, which may be made, for instance, by hydrogenation of a phthalic acid analog before esterification or a phthalate ester analog after esterification, and in which traces of the phthalate ester may be remaining) or the system may be completely free of phthalates, meaning that the composition consists of no phthalates, to the extent this can be determined by available technology.

In embodiments, there is also a composition comprising a plasticizable polymer and a plasticizing system comprising at least one ester of a polyol, whereby this polyol ester may be with short chain aliphatic acids, benzoic acid, and mixtures thereof, with or without a slower fusing plasticizer.

In preferred embodiments, the polymers may be selected from any known plasticizable polymer, preferably PVC, polyvinyl butyrals, polystyrenes, polyurethanes, acrylics, brominated rubbers, chlorinated rubbers, and polyolefins. Preferred polyolefins include polypropylene, EDPM, thermoplastic vulcanizates and thermoplastic elastomers.

In embodiments, the compositions including said plasticizable polymer comprise a plasticizing amount of said plasticizing system. The term "plasticizing amount" means an amount sufficient for the purpose of processing the polymer into a final article (such as a toy) or intermediate article (such as a pellet or powder) or the amount of plasticizer required to provide the finished article with the desired amount of softness or flexibility. One of skill in the art in possession of the present disclosure may determine the appropriate amount without more than routine experimentation. Minimum and maximum amounts suitable will vary depending on the plasticizer system, polymerizable polymer(s), additives, and process selected, among other reasons.

The plasticizer system may comprise one or more fast fusing plasticizers based on polyols and one or more slow fusing plasticizers. The terms "fast fusing plasticizer" and "slow fusing plasticizer" have been defined above. The fast fusing plasticizer may be used in amounts greater than or less than the total concentration of the slower fusing plasticizer.

The relative proportions of the plasticizers that are used will depend upon the desired properties of the processing and the final product. In embodiments, it is preferred to use at least 5 wt %, in other embodiments at least 10 wt %, in other embodiments at least 15 wt %, in other embodiments at least 20 wt %, in other embodiments at least 25 wt %, in other embodiments at least 30 wt %, in other embodiments at least 35 wt %, in other embodiments at least 40 wt %, in other embodiments at least 45 wt %, in other embodiments at least 50 wt %, in other embodiments at least 55 wt %, in other embodiments at least 60 wt %, in other embodiments at least 65 wt %, in other embodiments at least 70 wt %, in other embodiments at least 75 wt %, in other embodiments at least 80 wt %, in other embodiments at least 85 wt %, in other embodiments at least 90 wt %, of the plasticizer(s) of the invention, based on the total weight of plasticizer present. The remainder of the plasticizer system may preferably be the at least one slow fusing plasticizer, although other plasticizers may be included, such as other slow fusing plasticizers such as di-isononyl cyclohexandioates and/or even traditional phthalic acid ester plasticizers.

In embodiments, the plasticizer system may comprise no more than 95 wt % slow fusing plasticizer, in other embodiments no more than 90 wt %, or in other embodiments no more than 85 wt %, or in other embodiments no more than 80 wt %, or in other embodiments no more than 75 wt %, or in other embodiments no more than 70 wt %, or in other embodiments no more than 65 wt %, or in other embodiments no more than 60 wt %, or in other embodiments no more than 55 wt %, or in other embodiments no more than 50 wt %, or in other embodiments no more than 45 wt %, or in other embodiments no more than 40 wt %, or in other embodiments no more than 35 wt % or in other embodiments no more than 30 wt %, or in other embodiments no more than 25 wt %, or in other embodiments no more than 20 wt %. In embodiments, it is preferred to use at least 5 wt % of the slow fusing plasticizer, however in other embodiment preferred ranges include between 0.01 and 95 wt %, more preferably 5 to 90 wt %, in other embodiments 10 to 80 wt %, in other embodiments 20 to 70 wt %, in other embodiments 30 to 60 wt %. The fast fusing plasticizers may be present in these same percentages, e.g., 0.01 and 95 wt %, in other embodiments 5 to 90 wt %, in other embodiments 10 to 80 wt %, in other embodiments 20 to 70 wt %, or in other embodiments 30 to 60 wt %. DEHP (which, being the standard, is neither a fast nor a slow fusing plasticizer) may be used, along with phthalate ester plasticizer, and also more than one slow fusing plasticizers may be used.

In the plasticizer system comprising one or more fast fusing plasticizers based on the polyol esters of the invention and one or more slow fusing plasticizers, the slow fusing plasticizers are selected from esters of cyclohexanecarboxylic acids, preferably cyclohexanecarboxylic acid esters of C8 to C11 aliphatic alcohols, more preferably cyclohexanedicarboxylic acid esters of C8 to C11 aliphatic alcohols, which in embodiments will be C8-C11 aliphatic primary alcohols, more preferably 1,2-cyclohexanedicarboxylic acid esters of C8 to C11 aliphatic alcohols, more preferably 1,2 cyclohexanedicarboxylic acid esters of isononanol.

The term "cyclohexanecarboxylic acid" (as used herein) is intended to include the cyclohexane group having at least two carboxylic acid functional groups attached directly to the C6 ring, thus including dicarboxylic acid, tricarboxylic acids, and so on. All possible isomers of polycarboxylic acids are envisioned to be useful, however in preferred embodiments, the dicarboxylic acid isomer with the carboxylic acid groups in the 1,2-substitution position is the preferred isomer. Mixtures of isomers are also envisioned.

Note that cyclohexanecarboxylic acid esters may also be referred to as hexahydrophthalate esters.

The acid moiety of the fast fusing plasticizers of the present invention based on polyols are, as mentioned, short chain aliphatics, preferably C4-C9 acids but more preferably C6-C8 acids, which may be straight or preferably branched or a mixture thereof, and/or benzoic acid or derivatives thereof.

Blends of branched and linear acids, such as mixtures of C6 and C7 acids, each independently selected from branched and/or linear acids, or C7 and C8 acids, each independently selected from branched and/or linear alcohols, or C5 and C6 acids, each independently selected from branched and/or linear alcohols, or C4 and C5 acids, each independently selected from branched and/or linear alcohols, or C6, C7, and C8 acids, each independently selected from branched and/or linear alcohols, or C5, C6, and C7 acids, each independently selected from branched and/or linear alcohols, and so on, to encompass every possible mixture of C4-C9 acids, preferably C6-C8 acids, each independently selected from branched and/or linear alcohols, in each case wherein said acids are preferably branched acids, are also useful to make these plasticizers.

In embodiments the branched acids moiety has an overall branching (i.e., an average branching), as measured by NMR techniques, less than 1.8 branches per molecule, more preferably less than 1.5 branches per molecule, and still more preferably less than 1.4 branches per molecule. In preferred embodiments, the lower limit on branching is 0.8 branches per chain, on average. The NMR technique used to measure branching is per se known in the art. See, for instance, WO 2006012989.

For PVC plastisols the esters of this invention, in particular the fast fusing plasticizers, give lower plastisol viscosity and improved processability versus those prepared with plasticizers from cyclohexanecarboxylic acid esters alone, particularly the di-isononyl cyclohexanediacid ester or the di-2-ethylhexyl cyclohexanediacid ester or the di-2-propyl-heptyl cyclohexanediacid ester Plasticized polymer compositions according to embodiments of the invention offer advantages in other areas, such as in toy manufacturing, where the low viscosity and fusion properties would be an advantage over most alternatives, in automotive interior trim products because of their excellent UV stability, in extruded materials such as wire jacketing or tubing or hose or floor mats where the improved solvency and reduced fusion temperatures give high clarity products with low surface defects, in PVC film for uses such as wall paper or food containers or medical devices or stationary products, and in injection molded products for uses such as oxygen masks or cap liners or shoe soles. The fast fusing plasticiser according to the invention is especially beneficial as a non-yellowing viscosity modifier in vinyl sheet flooring manufacturing. In embodiments, the plasticizing system contributes to improved stain resistance. In a particularly preferred embodiment, the plasticizing system is useful as a process aid in the production of PVC toys through roto-molding and casting processes.

In an embodiment, the plasticizing system comprising at least one fast fusing plasticizer based on polyol esters of C4-C8 aliphatic acids, benzoic acids, or mixtures thereof may be mixed with plastics such as PVC in the amount of from 10 phr to 100 phr, where the descriptor phr refers to parts per hundred of resin or base polymer. Here, for example, 10 phr would refer to the weight of additive in pounds or kilos, in this case the plasticizer, added to 100 pounds or kilos of the PVC polymer.

In other embodiments, the plasticizing system of the invention may further comprise additives such as calcium carbonate fillers, Ca/Zn or Ba/Zn stabilizers, epoxidized soy bean oil, lubricants, pigments and dies or other colorants, antioxidants, and other stabilizers.

The PVC compositions of this invention can be processed into products through rotomolding, dipping, spraying, spreading, molding, extrusion, calendering, and injection molding, as well as by processing plastisols.

One widespread use of polyvinyl chloride is as a plastisol. A plastisol is a fluid or a paste consisting of a mixture of polyvinyl chloride and a plasticizer optionally containing various additives. A plastisol can be used to produce layers of polyvinyl chloride which are then fused to produce coherent articles of flexible polyvinyl chloride. Plastisols can be placed in cavity molds, then heated, to produced molded flexible PVC articles such as toys. Plastisols can be used to make gloves by dipping molds into the plastisol, and then heating. Plastisols are useful in the production of flooring, tents, tarpaulins, coated fabrics such as automobile upholstery, in car underbody coatings, in moldings and other consumer products. Plastisols are also used in footwear, fabric coating, toys, flooring products and wallpaper. Plastisols typically contain about 40 to about 200 parts by weight, more typically 50 to 150 parts by weight, more typically 70 to 100 parts by weight of plasticizer.

Plastisols are usually made from polyvinyl chloride that has been produced by emulsion polymerization or micro suspension polymerization. The plastisol may be produced by the manufacturer of the polyvinyl chloride or by a compounder, and be shipped to the user in fluid form. Alternatively the plastisol may be produced by the user. In either instance, although particularly when the plastisol is produced by the manufacture of the polyvinyl chloride or a compounder, it is important that the plastisol viscosity be stable over time.

In a further embodiment, the present invention provides a process for the production of flexible polyvinyl chloride comprising forming a layer from a plastisol containing from 40 to 200 parts by weight preferably 50 to 150 parts by weight, more preferably 70 to 120 parts by weight of a plasticizer composition of the invention, per 100 parts by weight of polyvinyl chloride, and subsequently fusing the layer by the application of heat.

Recent studies have identified that C7 to C8 tri esters of glycerol perform as general purpose (GP) plasticizers, having a good balance of efficiency, volatility, cost, compatibility, stability, and low temperature flexibility. The solution temperature or the ability of these particular GP plasticizers to dissolve the PVC resin can be improved through the use of lower C5 to C6 acids. However as the molecular weight of the acid side chains is reduced, the volatility of the plasticizer increases and the utility of fast fusing plasticizers produced through this path diminishes. So it is desired to improve the solvation strength of the plasticizer while maintaining good volatility.

Several recent reporting, as discussed in the background section, have described plasticizers produced with various polyol esters and blends of 2-EH acid and benzoic acid. Our work suggests that esters of 2-EH acid have reduced compatibility with PVC, leading to exudation. Partial replacement of 2-EH acid with benzoic acid will improve the compatibility of the plasticizer. Companies such as Ferro and LG have in fact filed patent applications on similar 2-EH acid/benzoic acid plasticizers and LG has at least one commercially available plasticizer believe to be produced from mixtures of 2-EH acid and benzoic acid. It has been explained above, however, that the 2-EH acid component of the ester is less desirable for reasons of toxicity concern. One patent, U.S. Pat. No. 6,740,254, mentions plasticizer esters based on C4 and benzoic acids.

Examples of where these fast fusing plasticizers products can be used:

TABLE 1

Automotive underbody sealants

| | |
|---|---|
| PVC copolymer | 100 |
| Invention plasticizer | 50 phr |
| DINP | 50 phr |
| Calcium carbonate | 100 phr |
| Other additives | 20 phr |

TABLE 2

Synthetic leather Top coat

| | |
|---|---|
| PVC | 100 |
| Invention plasticizer | 15 phr |
| DINP | 30 phr |
| Calcium carbonate | 5 phr |
| TXIB | 3 phr |
| Stabilizer | 3 phr |

TABLE 3

Synthetic leather Foam coat

| | |
|---|---|
| PVC | 100 |
| Invention plasticizer | 15 phr |
| DINP | 40 phr |
| Calcium carbonate | 20 phr |
| Stabilizer | 0.25 phr |
| Other additives | 2 phr |

TABLE 4

Floor mat clear

| | |
|---|---|
| PVC | 100 |
| Invention plasticizer | 20 phr |
| DIDP | 30 phr |
| Filler | 0 phr |
| Stabilizer | .3 phr |

TABLE 5

Wallpaper

| | |
|---|---|
| PVC | 100 |
| Invention plasticizer | 10 phr |
| DINP | 35 phr |
| Filler | 10 phr |
| Stabilizer | 2.3 phr |
| Lubricant | .25 phr |

TABLE 6

| Phthalate free rotomolded toy | |
| --- | --- |
| PVC Suspension resin | 100 |
| Invention plasticizer | 30 phr |
| Palatinol ® DINCH | 40 phr |
| Filler | 20 phr |
| Stabilizer | 3 phr |
| Other additives | 3 phr |

The fast fusing plasticizers and other polyol ester plasticisers according to the present invention may be incorporated in plastics (polymers). Preferred plastics are PVC, PVC modified with one or more comonomers (such as described in U.S. Pat. No. 3,583,956), PVB and PVB modified with one or more comonomers, homo- and copolymers based on ethylene, on propylene, on butadiene, on vinyl acetate, on glycidyl acrylate, on glycidyl methacrylate, or on acrylates having, bonded to the oxygen atom of the ester group, alkyl radicals of branched or unbranched alcohols having from 1 to 10 carbon atoms. The number of carbon atoms may be 2, 3, 4, 5, 6, 7, 8, and 9, including all ranges and subranges therebetween. Other preferred plastics are styrene, acrylonitrile, and homo- or copolymers of cyclic olefins.

Examples which may be mentioned of representatives of the above plastics groups are the following plastics: polyacrylates having identical or different alkyl radicals having from 4 to 10 carbon atoms bonded to the oxygen atom of the ester group, in particular having the n-butyl, n-hexyl, n-octyl, isononyl, or 2-ethylhexyl radical, polymethacrylate, polymethyl methacrylate, methyl acrylate-butyl acrylate copolymers, methyl methacrylate-butyl methacrylate copolymers, ethylene-vinyl acetate copolymers, chlorinated polyethylene, nitrile rubber, acrylonitrile-butadiene-styrene copolymers, ethylene-propylene copolymers, ethylene-propylene-diene copolymers, styrene-acrylonitrile copolymers, acrylonitrile-butadiene rubber, styrene-butadiene elastomers, methyl methacrylate-styrene-butadiene copolymers, and/or nitrolocellulose. The number of carbon atoms may be 5, 6, 7, 8, and 9, including all ranges and subranges therebetween.

PVC grades which may be used are suspension, bulk, microsuspension, and preferably emulsion PVC. Besides the esters described of cyclohexanedicarboxylic acid, phthalic acid, adipic acid, and benzoic acid, as well as other plasticizers, there may also be numerous other components known to the skilled worker added to the mixing specification. Examples of these are fillers, pigments, stabilizers, lubricants, blowing agents, kickers, antioxidants, biocides, etc.

The mixtures of the invention are preferably used for producing plastisols, in particular PVC plastisols, with particularly advantageous processing properties. These plastisols may be used in numerous products, such as synthetic leathers, flooring, or wallpapers, etc. Among these applications, particular preference is given to use in cushion vinyl (CV) flooring, and in particular here in the outer layer, where a further improvement is brought about in stain resistance. Use of the mixtures of the invention as a constituent in a mixing specification may provide plastisols having low viscosity and increased storage stability together with accelerated gelling and improved low-temperature flexibilization.

It is also possible for the nonylbenzoates or the above-mentioned mixtures of the invention with phthalates, with adipates, and/or with cyclohexanedicarboxylates, to be used as flexibilizers in coatings, paints, and inks, or components of adhesives.

Numerous esterification techniques are known in the art, e.g., such as disclosed in Volume 9 of the Kirk-Othmer Encyclopedia of Chemical Technology, Fourth Edition (1994), pp. 762-768. Preferred catalysts include titanium organometallic catalysts such as those per se well known in the art, e.g., U.S. Pat. No. 6,355,817 and U.S. Patent Applications No. 20050038283, WO2006125670, WO2008110305, and WO2008110306. It is also possible to prepare the fast fusing plasticizers of this invention without using catalysts.

The slow fusing plasticizers based on cyclohexanoate esters can be prepared from either esterification of the cyclohexane acids, diacids, or anhydrides with one or more of the desired alcohols or they can be prepared from hydrogenation of alcohol esters made from the corresponding aromatic acids or aromatic anhydrides such as phthalic anhydride, phthalic acid, isophthalic acid, terephthalic acid, or trimellitic anhydride. The 1,2-cyclohexane dicarboxylic acid anhydride or hexahydrophthalic anhydride, can be prepared through a direct route, such as the Diels Alder synthesis, using butadiene and maleic anhydride, followed by hydrogenation. In other embodiments, the slow fusing plasticizers esters can be prepared by esterification of hexahydrophthalic anhydride and/or hexahydroterephthalic acid with C8 to C10 alcohols. In other embodiments, the ester according to the invention can be prepared by direct esterification of C8-C11 alkenes with 1,2 hexahydrophthalic acid.

In preferred embodiments, the at least one C6 to C9 branched acids will be derived from a process comprising hydroformylation of an olefin, which may also be referred to as the oxonation reaction, and thus may be referred to herein as "oxo acids". The Oxo Process is per se well known. By way of recent examples of a high pressure Oxo processes, see, for instance, U.S. Pat. Nos. 7,345,212; 7,186,874; 7,148,388; 7,081,554; 7,081,553; 6,982,295; 6,969,736; 6,969,735; 6,013,851; 5,877,358; and PCT publications WO2007106215; WO2007040812; WO2006086067; WO2006055106; WO2003050070; WO2000015190. The aldehydes derived from the hydroformylation process starting from C5 to C8 olefins may be isolated from the hydroformylation product, preferably by distillation, and may then be oxidised to the corresponding acids, usually followed by a last distillation step to further purify the acids. The oxidation may be performed with or without a catalyst, and may use a suitable source of oxygen, preferably an oxygen-containing gas, more preferably air, which may be enriched with additional oxygen. Suitable aldehyde oxidation processes are known in the art. Processes to produce oxo alcohols are widely known and commercially practiced. It is possible to "retrofit" a process for oxo acids into such an oxo alcohol plant, by adding the equipment for distilling the hydroformylation product to isolate the aldehydes, for the oxidation step, usually requiring more than one reactor in series in order to achieve a higher single pass conversion, and for a final acid purification step, typically again by distillation. Such a "retrofit" approach would end up with a process similar to what is shown in FIG. 1. The high investment required in this route for the equipment required for distilling the aldehydes, for the oxidation, and for the final distillation, makes this route more preferred for large scale, high throughput deployment in continuous mode. Another drawback of this process is that the hydroformylation step may already produce significant amounts of alcohol and/or formate esters, which are typically converted to the alcohol by a hydrogenation step and generate an amount of oxo alcohol byproduct of the oxo acid process. If the aldehyde intermediate is isolated by distillation, the alkyl chains of the resulting oxo-acids may have different characteristics from those of the alcohol byproduct in this process, causing another possible element of complexity. The amount of alcohol byproduct may be significant and reduces the direct yield from the olefin starting material to the oxo acid. The overall acid yield may be improved when this process is combined with an oxidation step to convert at least part of the byproduct oxo alcohol to the corresponding oxo acid. The acid derived from this byproduct alcohol may however have different alkyl chain characteristics, and hence different properties, as the acids produced directly from the aldehyde intermediate.

The process of the invention may also comprise the hydroformylation of a lower olefin, such as ethylene, propylene, or one or more butenes selected from 1-butene, cis-2-butene, trans-2-butene and isobutene, or mixtures thereof. The hydroformylation of these olefins is preferably performed at lower pressure and with rhodium as the catalyst, typically in the form of a rhodium complex with a suitable ligand. Such processes are known in the art and examples are disclosed in U.S. Pat. No. 6,307,093, WO 2005095315, WO 2005095547, WO 2005028404 and WO 2005028407. The advantage of these hydroformylation processes, compared to the high pressure processes discussed before, is that they give a higher yield to the corresponding aldehydes, i.e. propionaldehyde from ethylene, n-butyraldehyde and isobutyraldehyde from propylene, n-pentanal and 2-methyl butanal from each of the n-butenes, and 3-methyl butanal from isobutene. These aldehydes, either in isolation or as a mixture of different aldehydes, may then be aldolised in order to produce an aldehyde having a higher carbon number, such as within the range of the present invention, aldolisation including the dehydration of the direct aldol product into the unsaturated aldehyde. When intended for oxidation to the acid, such unsaturated aldehyde is preferably first hydrogenated selectively to the corresponding saturated aldehyde, as this reduces the formation of byproducts during oxidation.

For example, propionaldehyde and one or more of the butyraldehydes may be aldolised together to produce an aldehyde mixture having an average carbon number of about 7, which is highly preferred as the intermediate for a branched C7 acid to form a polyol according to the present invention. The aldehyde product from aldolisation of propanal and butanals will contain the branched C6 aldehyde 2-methyl pentenal from the combination of two propanal molecules, branched C7 aldehydes from the condensation of propanal with one of the butanals, and C8 aldehydes from the condensation of two butanals. The average carbon number of the aldehyde mixture will be around 7, and there will be a significant presence of methyl branches. These alkyl chain characteristics are known to typically transfer unchanged onto the alcohol, through hydrogenation, and/or acid, through optional selective hydrogenation and oxidation, derived from the aldol product. N-butanal involved in the aldol condensation will lead to some ethyl branches in the product mixture, in particular on the $2^{nd}$ carbon from the oxygen, but the presence thereof is reduced as compared to pure 2-ethyl hexanol (2EH) or 2-ethyl hexanoic acid (2EH acid), which is advantageous because of the reduced toxicity concern.

In another preferred embodiment, butenes may be hydroformylated to a C5 aldehyde or a mixture thereof. A part of the C5 aldehyde(s) may then be converted, by one of the routes explained herein, to the corresponding C5 acid(s) which preferably at least partly contain methyl branching from either isobutylene in the feedstock or from the hydroformylation reaction itself as explained above. Another part of the C5 aldehyde or aldehyde mixture may be aldolised to a branched C10 aldehyde or aldehyde mixture, typically containing primarily 2-propyl branching but also containing minor amounts of methyl branching from methyl branches in the C5 aldehydes. When isobutylene is present in the starting butenes, the C10 products may have alkyl chains comprising isopropyl branching. A more detailed description of these C5 and C10 oxygenate products from butene hydroformylation is found in WO 2005028407. These C10 aldehyde(s) may then be converted to the corresponding C10 acid(s) by one of the routes explained herein. While a polyol such as a triglyceride produced from only C5 acids suffers from too high volatility and the equivalent from only C10 acid(s) from lack of resin compatibility, we have found that both these performance problems can be alleviated by using a mixture of the C5 acid(s) and the branched C10 acid(s) from this butene-based process, whereby the mixture has an average carbon number in the range of C6 to C9, as the branched acid for producing the polyol ester according to the invention, in particular the triglyceride ester. We have found that the content in the final polyol ester of the products causing the volatility or the compatibility problem is sufficiently reduced such that the problem may become insignificant, unnoticably small or even inexisting.

The branched aldehyde(s) from the direct hydroformylation of C5 to C8 olefins, or from the aldolisation of shorter chain aldehydes to branched aldehydes having average carbon numbers in the C6 to C9 range, may alternatively be hydrogenated to the corresponding alcohol(s) and subsequently be oxidized to the desired acid(s). The hydrogenation of such aldehydes is known in the art, and sufficiently explained in disclosures of the corresponding alcohol production processes, such as in the references cited above. The oxidation of such alcohol(s) to the aldehydes may be performed using a high temperature vapor phase process, but more preferably using a lower temperature liquid phase process. A suitable oxidation process may be found in the disclosure by Griffin et al, "Catalysts for selective oxidations", Specialty Chemicals Magazine, October 2001, page 13-14. In particular, the oxidation over a heterogeneous catalyst comprising platinum metal on carbon support, with air and at mild conditions of about 60° C. and 3 bar pressure, is preferred. The oxidation may be performed in two steps, the first step performing the oxidative dehydrogenation to produce the aldehyde as the major product, and the second step performing the oxidation of the aldehyde to the acid. The second step may then be performed as explained above, with but preferably without catalyst and preferably using air or enriched air as the source of oxygen. The process comprising the oxidation of the branched alcohol(s) to the acid(s) requires less additional equipment to be added to an existing oxo alcohol process, and is therefore preferred for producing smaller volumes of acids and/or polyol derivatives thereof. The relative proportion of the oxygenated molecules that is converted into acid(s), relative to what remains as alcohol(s) which may remain available for other derivatives, can then be chosen more freely. This reduces the amount of byproducts that may have to be discarded and increases overall yield to desirable products. Another advantage may be that the alcohol(s) and the acid(s) derived as coproducts by this process from the same feedstock typically have similar alkyl chains.

However, it will be recognized by one of skill in the art that branched acids may be derived from other processes.

The invention is also directed to the product of the process of the invention, which comprises at least one triglyceride compound according to structure (I) above, wherein at least one of the $R^1$, $R^2$, and $R^3$ groups defining the acids in the triglyceride is independently selected from C4 to C9 alkyl groups, whereby, if at least one of a C4 or a C9 alkyl group is present, this C4 to C9 group is present in a mixture of aliphatic acids, and whereby the mixture of aliphatic acids is having an average carbon number of at least 6 and at most 9, with the proviso that the average branching on the alkyl groups of the aliphatic acids is from about 0.5 to 3.0, preferably from 0.6 to 2.2. In an embodiment, the average branching may range from about 0.7 to about 1.8. In another embodiment, the average branching of the C5 to C8 alkyl groups ranges from about 0.8 to about 3.0, preferably around about 0.8 to about 1.6, more preferably about 1.2 to about 1.4 branches per molecule. These averages are based on the sum total of all alkyl groups on all $R^1$-$R^3$ side chains in all the polyols in the mixture.

The branches on the alkyl groups of the aliphatic acids in the products according to the invention comprise preferably at least 10% methyl branches, preferably at least 20% methyl branches, more preferably at least 40% or at least 50% methyl branches, even more preferably at least 60% or at least 70% methyl branches, and even more preferably at least 80% methyl branches. The amount of methyl branches on the alkyl chains may readily be determined by $^{13}$C-NMR techniques, if required by the 2-dimensional NMR techniques as explained in WO 2006/012989. If aryl groups or aryl acids are present, these are readily distinguished in these techniques from the alkyl groups, and evenly so for any alkyl substitution present in the aryl group. Preferably at most 95%, more preferably at most 90% and even more preferably at most 85% of the branches are methyl branches.

The average branching or branchiness may readily be determined by $^1$H-NMR analysis, which may be performed on the triglyceride ester, but may also be performed on the branched C6 to C9 acid prior to esterification or on the alcohol and/or aldehyde precursor thereof. It is known that the alkyl chain structures of the raw materials convert almost identically into the products during reactions such as esterification, especially if any excess raw materials are recovered and recycled, typically with little discard, during oxidation reactions and during hydrogenation reactions. If any differences can be identified, they are minor and negligible compared to structural changes that are known to occur during most oligomerisation reactions, the hydroformylation reaction, and the aldolisation reaction. Distillation may also provide a separation between isomers having different alkyl chain structures.

The branches in alkyl groups of the branched C6 to C9 aldehyde, the branched C6 to C9 alcohol, the branched C6 to C9 acid, the alkyl groups in the polyol ester derived therefrom, or in the triglyceride according to the invention, preferably are at least 20% methyl branches, more preferably at least 40% or at least 50% methyl branches, even more preferably at least 60% or at least 70% methyl branches, and even more preferably at least 80% methyl branches. The amount of methyl branches on the alkyl chains may readily be determined by $^{13}$C-NMR techniques, if required by the 2-dimensional NMR techniques as explained in WO 2006/012989. If aryl groups or aryl acids are present, these are readily distinguished from the alkyl groups, and evenly so for any alkyl substitution present in the aryl group.

The advantage of having a minimum methyl branching is that ethyl branching is reduced, in particular the presence of the 2-ethyl hexyl alkyl group on the acid part of the ester product. This is of interest because an ester, when introduced into a living organism such as a human or an animal, may become at least partly hydrolyzed. The ester hydrolysis liberates the acid. When the ester comprises high amounts of the 2-ethyl hexyl moiety on the acid alkyl group, 2-ethyl hexanoic acid is liberated in significant amounts in the organism, which is undesirable because of the toxicity concern associated with this specific acid (Manninen et al, 1989, Archives of Toxicology 63(2), pages 160-1). More preferably, the presence of the 2-ethyl hexyl group is further reduced by further increasing the presence of methyl branchiness in the alkyl chains. Most preferably the presence of the 2-ethyl hexyl group is avoided by excluding 2-ethyl hexanoic acid from the acids introduced into the esterification reaction step of the process of the invention producing the polyol ester, more specifically from the triglyceride according to the invention.

In the specific case of C7 triglycerides, the process of the invention provides, in preferred embodiments, an average branching of about 1.2±0.1, based on the branching in molecules having C7 acid groups and thus C6 alkyl chains in each of $R^1$, $R^2$ and $R^3$. In the specific case of C9 triglycerides, the process of the invention provides, in preferred embodiments, an average branching of about 3.0±0.1, based on the branching in molecules having C9 acid groups and thus C8 alkyl chains in each of $R^1$, $R^2$ and $R^3$. In a more preferred embodiment, there is a blend of triglycerides having a mixture of C7 and C9 acid groups and thus C6 and C8 alkyl chains on $R^1$, $R^2$ and $R^3$ resulting in an average branching of about 1.6±0.2, preferably 1.6±0.1.

The preferred C7 acid as intermediate for the polyol ester, and accordingly also the preferred triglyceride according to the invention, has an average carbon number from 6.5 to 7.5 and has, as determined by C13-NMR, from 5 to 20% of its first branch, counting from the oxygen in the acid or ester function, positioned on the second carbon, from 15 to 40% of the first branch positioned on the third carbon, and from 20 to 40% of the first branch positioned on the $4^{th}$ carbon position. More preferably, the branching is at least 60% methyl branching. The average branchiness of the aliphatic acid moiety preferably is between 1.0 and 1.4.

NMR analyses of the branching found in the oxo acids finds that these branches are typically methyl groups. For example, with the branched C8 oxo acid, typical isomers include 3-methyl heptanoic acid, 4-methyl heptanoic acid, 5-methyl heptanoic acid, as well as some 3,5-dimethyl hexanoic acid, 2,4 dimethyl hexanoic acid and 4,5 dimethyl hexanoic acid. Some n-octanoic acid is also present. Similar products are found with mixtures of isomers in the C7 or C9 oxo acids. C9 oxo acids when prepared from the OXO reaction using diisobutylene as the olefin feed will give mostly trimethyl branched acids, such a 3,5,5-trimethyl-hexanoic acid.

In the first step, branched aldehydes can be produced by hydroformylation of C5 to C8 higher olefins that in turn have been produced by propylene and/or butene oligomerization over solid phosphoric acid or zeolite catalysts. The oligomerization processes are per se well-known. See, for instance, U.S. Pat. Nos. 7,253,330, and 7,145,049.

The resulting C6 to C9 aldehydes can then be recovered from the crude hydroformylation product stream by fractionation to remove unreacted olefins and the corresponding alcohols.

These C6 to C9 aldehydes can then in turn be oxidized to their respective C6 to C9 acids using air or enriched air as an oxygen source. In the alternative, the C6 to C9 aldehydes can be hydrogenated to the corresponding alcohol and then fully oxidized to the acid by oxidation.

Following the oxidation reaction, the C6 to C9 acids can then be purified by fractionation to remove unreacted aldehydes and heavies formed during oxidation.

The C6 to C9 acids can then be esterified with glycerol or other alcohols including ethylene glycol, and other polyols.

Single carbon number acids can be used in the esterification, or acids of differing carbon numbers can be use to optimize product cost and performance requirements.

Glycerol is currently an attractive polyol for use to make plasticizers because it is abundantly available. It is, for instance, a major byproduct of biodiesel production. Other polyols, however, may be utilized to produce plasticizers, such as glycols, preferably ethylene glycol or propylene glycol. Mixtures of polyols may be used, such as a mixture of glycerol with propylene glycol.

It is preferred that the polyols be fully esterified so that there are a low to negligible amount of free hydroxyl groups. Thus, for example, it is preferred that glycerol is esterified to the triester.

The chemistry and a simplified process to produce triglycerides via the route described above is shown in equations (1)-(3), below. For simplicity, the hexene feed example is shown in eqn (1), but the feed can be pentenes, hexenes, heptenes, or octenes as the starting olefins. A mixture of branched hexenes is readily obtainable from the dimerisation of propylene. In the equations, the branchiness is shown as one methyl branch in a particular location, but the nature and location of the branch can be different, as illustrated by showing the methyl branch being in different positions in the different alkyl chains of the triglyceride product of equation (3). It is also noted that in the equations (1) to (3), the intermediates heptanal and heptanoic acid are erroneously pictured as branched octanal and octanoic acid. As discussed above, the resulting C6, C7, C8, and C9 acids may be used individually or together in mixtures to make mixed carbon number esters to be used as plasticizers. This mixing of carbon numbers and levels of branching may be manipulated to achieve the desired compatibility with PVC for the respective polyol used for the polar end of the plasticizer, and to meet other plasticizer performance properties.

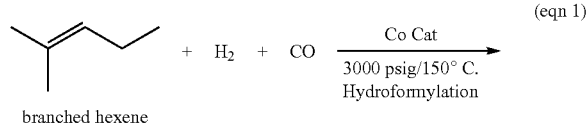

(eqn 1)

branched hexene, Co Cat, 3000 psig/150° C. Hydroformylation, heptanal

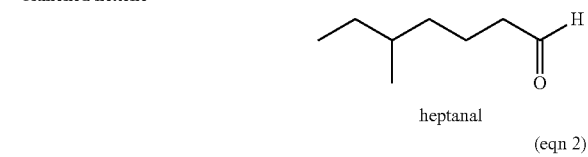

(eqn 2)

heptanal, O₂(Air), No Cat, 45 psig/40° C. Oxidation, heptanoic acid

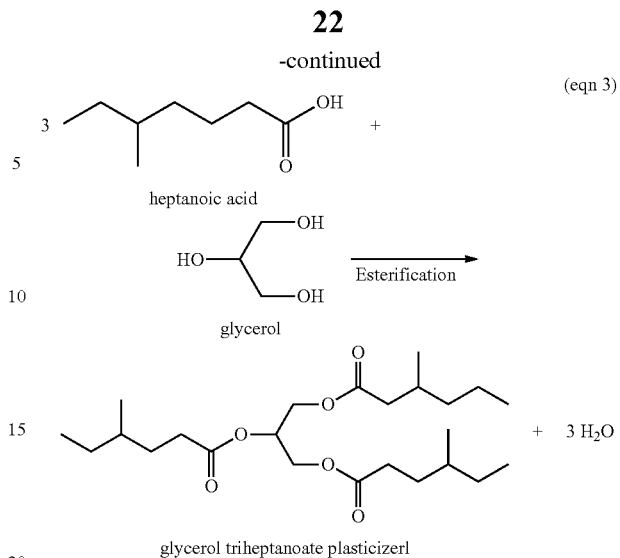

(eqn 3)

heptanoic acid + glycerol → Esterification → glycerol triheptanoate plasticizer1 + 3 H₂O The applicability of the triglyceride structures as potential PVC plasticizers can be screened by estimating their relative solubility in PVC using Small's group contribution method to calculate solubility parameters for each structure (see The Technology of Plasticizers by J. Sears and J. Darby, John Wiley & Sons, New York, 1982, pp 95-99, discussing using the Small formula to looking at plasticizer compatibility with PVC; this paper sites as a reference, the original work by Small: Small, P. A., "Some Factors Affecting the Solubility of Polymers", J. Appl. Chem., 3, pp 76-80 (1953); see also using Small's group contribution values from the Polymer Handbook, 3rd Ed., J. Brandrup & E. H Immergut, Eds. John Wiley, New York, (1989)). These calculations are shown below in Table 7 for the C6 triglyceride:

TABLE 7

| C6 Triglyceride | | | | | |
|---|---|---|---|---|---|
| | Solubility | Number | Solubility Contrib | MW | MW Contrib |
| CH3 | 214 | 6 | 1284 | 15 | 90 |
| —CH2— | 133 | 8 | 1064 | 14 | 112 |
| —CH= | 28 | 4 | 112 | 13 | 52 |
| COO esters | 310 | 3 | 930 | 44 | 132 |
| | | | 3390 | | 386 |
| | Solubility Parameter = | | 8.43 | Density = | 0.96 |
| | Delta to PVC = | | −1.23 | | |

Likewise, they may also be calculated for the C7 triglyceride, shown in Table 8:

TABLE 8

| C7 Triglyceride | | | | | |
|---|---|---|---|---|---|
| | Solubility | Number | Solubility Contrib | MW | MW Contrib |
| CH3 | 214 | 6 | 1284 | 15 | 90 |
| —CH2— | 133 | 11 | 1463 | 14 | 154 |
| —CH= | 28 | 4 | 112 | 13 | 52 |
| COO esters | 310 | 3 | 930 | 44 | 132 |
| | | | 3789 | | 428 |
| | Solubility Parameter = | | 8.50 | Density = | 0.96 |
| | Delta to PVC = | | −1.16 | | |

Table 9 shows the values calculated by the same method for the C8 triglyceride:

TABLE 9

C8 Triglyceride

|  | Solubility | Number | Solubility Contrib | MW | MW Contrib |
|---|---|---|---|---|---|
| CH3 | 214 | 6 | 1284 | 15 | 90 |
| —CH2— | 133 | 14 | 1862 | 14 | 196 |
| —CH= | 28 | 4 | 112 | 13 | 52 |
| COO esters | 310 | 3 | 930 | 44 | 132 |
|  |  |  | 4188 |  | 470 |
| Solubility Parameter = |  | 8.55 | Density = | 0.96 |  |
| Delta to PVC = |  | −1.11 |  |  |  |

Table 10 shows the values calculated by the same method for the C9 triglyceride:

TABLE 10

C9 Triglyceride

|  | Solubility | Number | Solubility Contrib | MW | MW Contrib |
|---|---|---|---|---|---|
| CH3 | 214 | 6 | 1284 | 15 | 90 |
| —CH2— | 133 | 17 | 2261 | 14 | 238 |
| —CH= | 28 | 4 | 112 | 13 | 52 |
| COO esters | 310 | 3 | 930 | 44 | 132 |
|  |  |  | 4587 |  | 512 |
| Solubility Parameter = |  | 8.6 | Density = | 0.96 |  |
| Delta to PVC = |  | −1.06 |  |  |  |

The solubility parameter of PVC is calculated by the same Small's Group Contribution Method to be 9.66. The differences in solubility parameters between the triglyceride structures in Formula I and PVC are shown in Tables 7-10. These differences from PVC range from 1.23 for the C6 triglyceride to 1.06 units for the C9 triglyceride, which indicates reasonable expected solubility in PVC for these materials. As references, the solubility parameters for two well-known phthalate plasticizers, di-isononyl phthalate (DINP) and di-isodecyl phthalate (DIDP) are 8.88 (delta to PVC=0.78), and 8.56 (delta to PVC=1.10) respectively. The estimated solubility parameter for one non-phthalate plasticizer, di-isononyl cyclohexanoate, is 7.32 by Small's method. This is a difference of 2.34 solubility parameter units from PVC.

An illustration of an embodiment of the invention is illustrated in FIG. 1. Propylene is used as feedstock to an oligomerization reaction. The reaction may be continuous, batch, or semibatch. Unreacted C3 olefins are distilled off and optionally recycled. Trimers and tetramers may be recovered as bottoms product with the desired dimer hexene taken as a sidestream and send to the hydroformylation reaction. Carbon monoxide and hydrogen, conveniently supplied as Syngas, are also supplied to the reactor. The products are then separated by fractionation, with light olefins optionally recycled and the C7 aldehydes and C7 alcohols being separated. The amount of aldehyde and alcohols produced may be attenuated in the hydrofinishing section. In an embodiment, the C7 aldehydes are then oxidized with the addition of air and/or oxygen, and unreacted aldehydes and heavies are separated out. The desired product C7 acid is then esterified with polyol, in this embodiment glycerol and recovered as the triglyceride.

The plasticizers according to the invention may also be used with vinyl chloride-type resins, polyesters, polyurethanes, ethylene-vinyl acetate copolymer, rubbers, acrylics, polymer blends such as of polyvinyl chloride with an ethylene-vinyl acetate copolymer or polyvinyl chloride with a polyurethane or ethylene-type polymer.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The invention has been described above with reference to numerous embodiments and specific examples. Many variations will suggest themselves to those skilled in this art in light of the above detailed description. All such obvious variations are within the full intended scope of the appended claims.

The present invention is now illustrated by the following examples.

EXAMPLES

Comparative Example 1

A mixture comprising 100 grams of glycerol tris-2-ethylhexanoate, 0.5 grams stearic acid, 4 grams of epoxidized soybean oil, and 5 grams of the Calcium/Zinc PVC stabilizer Mark 1221 (from Chemtura) was slowly heated to 50° C. on a hot plate, with stirring, until the stearic acid dissolved. The solution was cooled to room temperature, then slowly poured over 200 grams of PVC resin (Oxy 240) and mixed in a Hobart mixer for 5 minutes. The powder mixture was then heated on a roll mill, at 165° C. for 5 minutes. The sheets from the roll mill were then compression molded at 171° C., first at 1000 psig, then at 3500 psig. After cooling the sheets were removed for testing.

In the case of the glycerol tris-2-ethylhexanoate, after 4 days of conditioning at 22° C. and 50% relative humidity a heavy level of exudation was observed on the surface of the flexible PVC films. Testing of the material was discontinued. Glycerol tris-2-ethylhexanoate is based on a branched C8 acid having 100% ethyl branches and 0% methyl branches on its alkyl chains.

Comparative Example 2

A mixture comprising 100 grams of glycerol tris-isononanoate, 0.5 grams stearic acid, 4 grams of epoxidized soybean oil, and 5 grams of the Calcium/Zinc PVC stabilizer Mark 1221 (from Chemtura) was slowly heated to 50° C. on a hot plate, with stirring, until the stearic acid dissolved. The solution was cooled to room temperature, then slowly poured over 200 grams of PVC resin (Oxy 240) and mixed in a Hobart mixer for 5 minutes. The powder mixture was then heated on a roll mill, at 165 C for 5 minutes. The sheets from the roll mill were then compression molded at 171° C., first at 1000 psig, then at 3500 psig. After cooling the sheets were removed for testing.

In the case of the glycerol tris-isononanoate, after 4 days of conditioning at 22° C. and 50% relative humidity a heavy level of exudation was observed on the surface of the flexible PVC films. Testing of the material was discontinued. The glycerol tris-isononanoate in this example is based on isononanoic acid containing 97.5% wt of 3,5,5-trimethyl hexanoic acid, a triple branched C9 acid having 100% methyl branches.

Comparative Example 3

A mixture comprising 100 grams of the glycerol tri ester prepared from a 50/50 mixture on n-octanoic acid and n-decanoic acid, together with 0.5 grams stearic acid, 4 grams of epoxidized soybean oil, and 5 grams of the Calcium/Zinc PVC stabilizer Mark 1221 (from Chemtura) was slowly heated to 50° C. on a hot plate, with stirring, until the stearic acid dissolved. The solution was cooled to room temperature, then slowly poured over 200 grams of PVC resin (Oxy 240) and mixed in a Hobart mixer for 5 minutes. The powder mixture was then heated on a roll mill, at 165° C. for 5 minutes. The sheets from the roll mill were then compression molded at 171° C., first at 1000 psig, then at 3500 psig. After cooling the sheets were removed for testing.

In the case of this glycerol ester, after 24 hours of conditioning at 22° C. and 50% relative humidity a very heavy level of exudation was observed on the surface of the flexible PVC films and the films turned opaque. Further testing of the material was discontinued due to the incompatibility of the plasticizer with the PVC. The glycerol ester in this example is based on a mixture of unbranched acids having an average carbon number of 9.

Example 4

A mixture comprising 100 grams of glycerol tris-isoheptanoate, 0.5 grams stearic acid, 4 grams of epoxidized soybean oil, and 5 grams of the Calcium/Zinc PVC stabilizer Mark 1221 (from Chemtura) was slowly heated to 50° C. on a hot plate, with stirring, until the stearic acid dissolved. The solution was cooled to room temperature, then slowly poured over 200 grams of PVC resin (Oxy 240) and mixed in a Hobart mixer for 5 minutes. The powder mixture was then heated on a room mill, at 165° C. for 5 minutes. The sheets from the roll mill were then compression molded at 171° C., first at 1000 psig, then at 3500 psig. After cooling the sheets were removed for testing.

The PVC specimens were conditioned for 7 days at 22° C. and 50% relative humidity before testing. The following properties were recorded for the isoC7 triglyceride ester in this PVC formulation: Shore A Hardness (15 sec) 76; tensile strength 3144 psi, elongation 394%, weight loss after 7 days at 100° C. 10.9%, carbon volatility loss after 24 hrs at 70° C. of 0.05%.

Example 5

A mixture comprising 80 grams of glycerol tris-isoheptanoate, 0.5 grams stearic acid, 4 grams of epoxidized soybean oil, and 5 grams of the Calcium/Zinc PVC stabilizer Mark 1221 (from Chemtura) was slowly heated to 50° C. on a hot plate, with stirring, until the stearic acid dissolved. The solution was cooled to room temperature, then slowly poured over 200 grams of PVC resin (Oxy 240) and mixed in a Hobart mixer for 5 minutes. The powder mixture was then heated on a room mill, at 165° C. for 5 minutes. The sheets from the roll mill were then compression molded at 171 C, first at 1000 psig, then at 3500 psig. After cooling the sheets were removed for testing.

The PVC specimens were conditioned for 7 days at 22° C. and 50% relative humidity before testing. The following properties were recorded for the isoC7 triglyceride ester in this PVC formulation: Shore A Hardness (15 sec) 86; tensile strength 1968 psi, elongation 353%, Clashberg $T_f$ of −22° C., and Bell Brittleness temperature $T_b$ of −38° C.

Example 6

A mixture comprising 100 grams of glycerol tris-(isoheptanoate/benzoate), 0.5 grams stearic acid, 4 grams of epoxidized soybean oil, and 5 grams of the Calcium/Zinc PVC stabilizer Mark 1221 (from Chemtura) was slowly heated to 50° C. on a hot plate, with stirring, until the stearic acid dissolved. The solution was cooled to room temperature, then slowly poured over 200 grams of PVC resin (Oxy 240) and mixed in a Hobart mixer for 5 minutes. The powder mixture was then heated on a room mill, at 165° C. for 5 minutes. The sheets from the roll mill were then compression molded at 171° C., first at 1000 psig, then at 3500 psig. After cooling the sheets were removed for testing.

The PVC specimens were conditioned for 7 days at 22° C. and 50% relative humidity before testing. No exudation was observed. The following properties were recorded for the iso C7 triglyceride/benzoate tri ester in this PVC formulation:

Shore A Hardness (15 sec) 74; tensile strength 2982 psi, elongation 381%, weight loss after 7 days at 100° C. 8.4%, carbon volatility loss after 24 hrs at 70° C. of 0.05%, low temperature flexibility by the Clashberg method of −31° C.

Examples 1-3 illustrate that triglycerides with 2-ethyl hexanoic acid, with the triple branched C9 acid and with a 50/50 mix of normal C8 and C10 acid have a disadvantage in terms of limited compatibility with PVC resin. Examples 4-6 illustrate that a TGE of branched C7 acid does not have that disadvantage. This acid has an average carbon number of 7, an average branching of about 1.2 per molecule, and 60+% of the branches being methyl branches. When also benzoic acid is incorporated in the TGE, the compatibility remains acceptable and plasticizing efficiency is increased.

Examples 7-16

To a 50 ml beaker was added 24 grams of plasticizer and 1 gram of PVC resin (Oxy 240). The beaker was placed on a hotplate with magnetic stirring and slowly heated at approximately 3 g/minute until the PVC resin dissolved in the plasticizer. This clear point is defined as the solution temperature.

With this method, the following data was obtained:

| | |
|---|---|
| Ex 7: Diisononyl phthalate | 123° C. |
| Ex 8: Cyclohexane dicarboxylic acid of isononanol | 135° C. |
| Ex 9: Glycerol tris-2-ethyl hexanoate | 166° C. |
| Ex 10: Glycerol tris isoheptanoate | 139° C. |
| Ex 11: Glycerol tris isononanoate | >170° C. (PVC decomposition) |
| Ex 12: Glycerol tris (2-ethylhexanoate/benzoate) | 124° C. |

| | |
|---|---|
| Ex 13: Glycerol tris (isononanoate/benzoate) | 137° C. |
| Ex 14: Glycerol tris (isoheptanoate/benzoate) | 112° C. |
| Ex 15: Glycerol tris (isohexanoate/isononanoate) | 155° C. |
| Ex 16: Glycerol tris (pentanoate/isopentanoate/2-propyl heptanoate) | 141° C. |

These examples illustrate how the acid part of the triglyceride may be selected in order to achieve certain desired fusing properties.

Examples 17-19

To a 500 ml beaker was added 100 grams of plasticizer, 6 grams of Drapex 6.8 ESO co-stabilizer, 5 grams of Baerostab XCT stabilizer and 0.5 grams of stearic acid. The mixture was slightly warmed with light stirring until all the solids had dissolved, then cooled to room temperature. This solution was slowly poured over 200 grams of Oxy 240 suspension grade PVC resin with moderate stirring for 5 minutes via a Hobart mixer.

A weighed portion of this mixture was then placed in a Braebender Plasti-corder with a sigma mixing head, preheated to 88° C. After 1 minute of preheat time, the sample was mixed at 60 rpm's, until a dryblend was obtained.

Using this procedure, the following plasticizer absorption time was obtained for the following 3 plasticizers. Jayflex DINP is a di-isononyl phthalate plasticiser obtainable from ExxonMobil Chemical, and a prime example of a general purpose PVC plasticiser. Hexamol DINCH is a diester of isononyl alcohol with 1,2-cyclohexane dicarboxylic acid, and is one of the attempts in order to find a phthalate substitute.

| | |
|---|---|
| Ex 17: Jayflex DINP | 3.26 minutes |
| Ex 18: Hexamol DINCH | 4.16 minutes |
| Ex 19: Glycerol tris isoheptanoate | 3.25 minutes |

These examples illustrate that a triglyceride with a branched C7 acid may perform very comparatively to a DINP, and even outperform the other proposed phthalate substitute.

The invention claimed is:

1. A composition comprising a triglyceride according to the formula

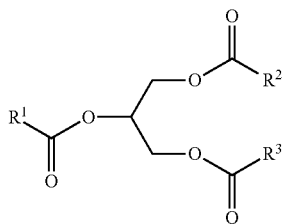

wherein $R^1$, $R^2$, and $R^3$ are alkyls, and at least one of the $R^1$, $R^2$, and $R^3$ groups defining the acid moieties in the triglyceride, is independently selected from C4 to C9 alkyl groups, whereby, if at least one of a C4 or a C9 alkyl group is present, this C4 or C9 group is present in a mixture of aliphatic acids, and whereby the mixture of aliphatic acids has an average carbon number of at least 6 and at most 9, with the proviso that the average branching on the alkyl groups of the aliphatic acid moieties is from 0.5 to 3.0 per molecule, and wherein at least 10% of the branches on the alkyl groups of the aliphatic acid moieties are methyl branches.

2. A composition comprising PVC and the composition according to claim 1.

3. The composition according to claim 1 wherein each of $R^1$, $R^2$, and $R^3$ is a C6 alkyl group, and wherein the average branching is about 1.2±0.1 per molecule, and wherein the branches are selected from methyl and a combination of methyl and ethyl branches.

4. The composition according to claim 1 wherein at least one of the acid moieties has an average carbon number from 6.5 to 7.5 and has, as determined by C13-NMR, from 5 to 20% of its first branch, counting from the oxygen in the acid or ester function, on the second carbon, from 15 to 40% of the first branch on the third carbon, and from 20 to 40% of the first branch on the $4^{th}$ carbon.

5. The composition according to claim 1 further comprising a phthalate plasticiser.

6. A method of using the composition according to claim 1 as a fast fusing plasticiser.

7. The composition according to claim 1, wherein the average branching of the alkyl groups of the aliphatic acid moieties is from 0.6 to 2.2 per molecule.

8. The composition according to claim 1, wherein the average branching of the alkyl groups of the aliphatic acid moieties is from 0.7 to 1.8 per molecule.

9. The composition according to claim 1, wherein the average branching of the alkyl groups of the aliphatic acid moieties is from 0.8 to 1.6 per molecule.

10. The composition according to claim 1, wherein the average branching of the alkyl groups of the aliphatic acid moieties is from 1.2 to 1.4 per molecule.

11. The composition according to claim 1, wherein at least 50% of the branches on the alkyl groups of the aliphatic acid moieties are methyl branches.

12. The composition according to claim 1, wherein at least 80% of the branches on the alkyl groups of the aliphatic acid moieties are methyl branches.

13. The composition according to claim 5, wherein the phthalate plasticiser is selected from the group consisting of di-isononyl phthalate, di-isodecyl phthalate, di-2-propylheptyl phthalate, di-isoundecyl phthalate, di-2-ethylhexyl phthalate, and mixtures thereof.

* * * * *